United States Patent [19]

Austel et al.

[11] Patent Number: 4,568,680
[45] Date of Patent: Feb. 4, 1986

[54] 2-PHENYL-IMIDAZO[4,5-C]PYRIDINONES USEFUL AS CARDIOTONIC AGENTS

[75] Inventors: Volkhard Austel; Norbert Hauel, both of Biberach; Joachim Heider, Warthausen; Manfred Reiffen, Biberach; Jacobus C. A. Van Meel, Biberach; Willi Diederen, Biberach, all of Fed. Rep. of Germany

[73] Assignee: Dr. Karl Thomae GmbH, Biberach an der Riss, Fed. Rep. of Germany

[21] Appl. No.: 678,235

[22] Filed: Dec. 5, 1984

[30] Foreign Application Priority Data

Dec. 23, 1983 [DE] Fed. Rep. of Germany ....... 3346602

[51] Int. Cl.$^4$ .................... A01N 43/40; C07D 491/02
[52] U.S. Cl. ..................................... 514/303; 546/118
[58] Field of Search ......................... 546/118; 514/303

[56] References Cited

U.S. PATENT DOCUMENTS 3,932,428  1/1976  Doherty ............................. 546/118

Primary Examiner—Henry R. Jiles
Assistant Examiner—J. Richter
Attorney, Agent, or Firm—Hammond & Littell, Weissenberger & Dippert

[57] ABSTRACT

Compounds of the formula

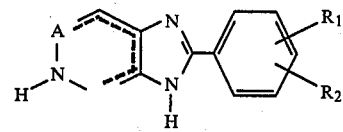

wherein one of A and B is methenyl (—CH=) and the other is carbonyl;

$R_1$ is (alkyl of 1 to 3 carbon atoms)mercapto, (alkyl of 1 to 3 carbon atoms)sulfinyl or (alkyl of 1 to 3 carbon atoms)sulfonyl; and $R_2$ is alkoxy of 1 to 3 carbon atoms;

tautomers thereof, and non-toxic, pharmacologically acceptable acid addition salts thereof. The compounds are useful as cardiotonics.

5 Claims, No Drawings

2-PHENYL-IMIDAZO[4,5-C]PYRIDINONES USEFUL AS CARDIOTONIC AGENTS

This invention relates to novel 2-Phenyl-imidazo-[4,5-c] pyridinones and their non-toxic acid addition salts, to methods of preparing these compounds, to pharmaceutical compositions containing them as active ingredients, and to a method of using them as cardiotonics.

More particularly, the present invention relates to a novel class of compounds represented by the formula

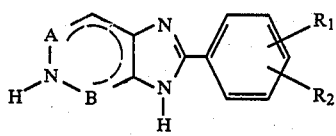

wherein one of A and B is methenyl (—CH=) and the other is carbonyl;
R₁ is (alkyl of 1 to 3 carbon atoms) mercapto, (alkyl of 1 to 3 carbon atoms) sulfinyl or (alkyl of 1 to 3 carbon atoms) sulfonyl; and
R₂ is alkoxy of 1 to 3 carbon atoms;
tautomers thereof; and non-toxic, pharmacologically acceptable acid addition salts thereof.

Examples of specific embodiments of substituents R₁ and R₂ are the following:
R₁: Methylmercapto, ethylmercapto, n-propylmercapto, isopropylmercapto, methylsulfinyl, ethylsulfinyl, n-propylsulfinyl, isopropylsulfinyl, methylsulfonyl, ethylsulfonyl, n-propylsulfonyl or isopropylsulfonyl.
R₂: Methoxy, ethoxy, n-propoxy or isopropoxy.

A preferred subgenus is constituted by those compounds of the formula I
where
R₁ is in the 4-position of the phenyl ring, and
R₂ is in the 2-position of the phenyl ring,
tautomers thereof, and non-toxic, pharmacologically acceptable acid addition salts thereof.

The compounds embraced by formula I may be prepared by the following methods:

Method A

By cyclizing a compound of the formula

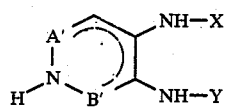

wherein
one of A' and B' is methenyl and the other is carbonyl or (alkoxy of 1 to 3 carbon atoms)-methenyl, and
one of X and Y is hydrogen and the other or both are

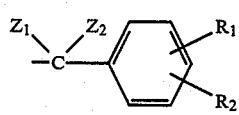

where
R₁ and R₂ have the meanings previously defined; and $Z_1$ and $Z_2$, which may be identical to or different from each other, are each independently halogen, optionally substituted amino, hydroxyl, lower alkoxy, mercapto or lower alkyl-mercapto; or
$Z_1$ and $Z_2$ together are oxygen, sulfur, imino, mono- or di-(alkyl of 1 to 3 carbon atoms) imino, alkylenedioxy of 2 or 3 carbon atoms or alkylenedithio of 2 or 3 carbon atoms.

The starting compounds of the formula II may be prepared separately or in situ in the reaction mixture.

The cyclization is advantageously carried out in a solvent or mixture of solvents such as ethanol, isopropanol, glacial acetic acid, benzene, chlorobenzene, toluene, xylene, glycol, glycol monomethyl ether, diethylene glycol dimethyl ether, sulpholane, dimethylformamide or tetralin, or in an excess of the acylating agent which is used to prepare the compound of the formula II, for instance in the corresponding nitrile, anhydride, acid halide, ester, amide or methiodide, at temperatures between 0° and 250° C., but preferably at the boiling point of the reaction mixture, optionally in the presence of a condensing agent such as phosphorus oxychloride, thionyl chloride, sulfuryl chloride, sulfuric acid, p-toluenesulfonic acid, hydrochloric acid, phosphoric acid, polyphosphoric acid, acetic anhydride, or possibly in the presence of a base such as potassium ethoxide or potassium tert. butoxide. However, the cyclization may also be carried out without a solvent and/or condensing agent.

If a compound of the formula II wherein one at A' and B' is alkoxymethyl is used, the alkoxymethenyl group may also be converted during the reaction or subsequently into a carbonyl group, for instance by acid or alkaline hydrolysis. Advantageously, the subsequent hydrolysis is carried out in the presence of an acid such as sulfuric acid, hydrochloric acid, phosphoric acid or p-toluenesulfonic acid at temperatures between 80° and 120° C.

Method B

By oxidizing a compound of the formula

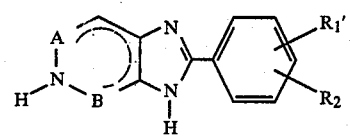

wherein
A, B and R₂ have the meanings previously defined, and
R₁' is (alkyl of 1 to 3 carbon atoms) mercapto or (alkyl of 1 to 3 carbon atoms) sulfonyl.

The oxidation is preferably carried out in a solvent or mixture of solvents, for instance in water, water/pyridine, acetone, glacial acetic acid, dilute sulfuric acid or trifluoroacetic acid, advantageously at temperatures between —80° and 100° C., depending upon the particular oxidizing agent which is used.

In order to prepare an alkylsulfinyl compound of the formula I, the oxidation is carried out with one equivalent of the oxidizing agent, for example with hydrogen peroxide in glacial acetic acid, trifluoroacetic acid or formic acid at 0° to 20° C. or in acetone at 0° to 60° C.; with a peracid such as performic acid in glacial acetic acid or trifluoroacetic acid at 0° to 50° C. or with m-chloroperbenzoic acid in methylene chloride or chloroform at −20° to 60° C.; with sodium metaperiodate in aqueous methanol or ethanol at −15° to 25° C.; with bromine in glacial acetic acid or aqueous acetic acid; with N-bromo-succinimide in ethanol; with tert. butyl hypochlorite in methanol at −80° to −30° C.; with iodobenzodichloride in aqueous pyridine at 0° to 50° C.; with nitric acid in galcial acetic acid at 0° to 20° C.; with chromic acid in glacial acetic acid or in acetone at 0° to 20° C.; or with sulfuryl chloride in methylene chloride at −70° C., and the thioether-chlorine complex thus obtained is hydrolyzed with aqueous ethanol.

In order to prepare an alkylsulfonyl compound of the formula I, the oxidation is carried out with one or with two or more equivalents of the oxidizing agent, for instance with hydrogen peroxide in glacial acetic acid, trifluoroacetic acid or formic acid at 20° to 100° C. or in acetone at 0° to 60° C.; with a peracid such as performic acid or m-chloroperbenzoic acid in glacial acetic acid, trifluoroacetic acid, methylene chloride or chloroform at temperatures between 0° and 60° C.; with nitric acid in glacial acetic acid at 0° to 20° C.; with chromic acid or potassium permanganate in glacial acetic acid, water/sulfuric acid or in acetone at 0° to 20° C.

The compounds embraced by formula I are basic and therefore form addition salts with inorganic or organic acids. Examples of non-toxic, pharmacologically acceptable acid addition salts are those formed with hydrochloric, hydrobromic, sulfuric, phosphoric, fumaric, succinic, tartaric, citric, lactic, maleic or methanesulfonic acid.

The starting compounds of the formulas II and III are either disclosed in the literature or may be prepared by methods described in the literature. For example, the starting compounds of the formula II are obtained by acylating the corresponding o-diamino compounds or by reducing the corresponding acylaminonitro compounds, and the compounds of the formula III are obtained by subsequent cyclization (see British Pat. No. 810,545 and Published European Application No. 24,290) of a corresponding compound of the formula II. The starting compound used in Example 2, namely, 2-methoxy-3,4-diamino-pyridine is described in J. Chem. Soc. 1971, 1432. The starting compound used in step (a) of Example 1 was prepared, starting from compound VI shown on page 197 of J. Het. Chem., vol. 2 (1965), by alkaline hydrolysis analogous to the preparation of 2-amino-4-hydroxy-pyridine described in J. Chem. Soc. 1971, 1432.

The following examples illustrate the present invention and will enable others skilled in the art to understand it more completely. It should be understood, however, that the invention is not limited solely to the particular examples given below.

EXAMPLE 1

2-(2-Methoxy-4-methylmercapto-phenyl)-5H-imidazo[4,5-c]-pyridin-6-one (a) 4-(2-Methoxy-4-methylmercapto-benzoylamino)-5-nitro-1H-pyridin-2-one A mixture of 0.45 g of 4-amino-5-nitro-1H-pyridin-2-one and 0.87 g of 2-methoxy-4-methylmercapto-benzoyl chloride was refluxed for 8 hours in 10 ml of chlorobenzene. The precipitated product was suction-filtered off, washed with methylene chloride and used in the next step as the crude product without further purification.

Yield: 0.72 g (57% of theory).

(b) 2-(2-Methoxy-4-methylmercapto-phenyl)-5H-imidazo[4,5-c]-pyridin-6-one 0.6 g of crude 4-(2-methoxy-4-methylmercapto-benzoylamino)-5-nitro-1H-pyridin-2-one were dissolved in 10 ml of glacial acetic acid, the solution was mixed with two spatula tipsful of iron powder, and the mixture was stirred for 30 minutes at room temperature. The mixture was then refluxed for 20 minutes, filtered, and the filtrate was evaporated in vacuo. The product thus obtained were purified by chromatography on silica gel (eluant: methylene chloride/ethanol=100:2 to 100:15).

Yield: 0.13 g (22% of theory).

Melting point: 236°–238° C.

EXAMPLE 2

2-(2-Methoxy-4-methylmercapto-phenyl)-5H-imidazo[4,5-c]pyridin-4-one 0.88 g of 2-methoxy-3,4-diamino-pyridine hydrochloride and 1.08 g of 2-methoxy-4-methylmercapto-benzoyl chloride were intimately mixed, and the mixture was stirred into warm polyphosphoric acid at 120° C. The mixture was kept at this temperature for an hour and was then poured into water, the aqueous mixture was made alkaline with ammonia, and the precipitate thus obtained was purified on a silica gel column (eluant: methylene chloride/methanol=100:10).

Yield: 0.22 g (15% of theory).

Melting point: 243°–245° C.

EXAMPLE 3

2-(2-Methoxy-4-methylsulfinyl-phenyl)-5H-imidazo[4,5-c]pyridin-4-one 0.3 g of 2-(2-methoxy-4-methylmercapto-phenyl)-5H-imidazo[4,5-c]pyridin-4-one were suspended in 10 ml of 50% acetic acid, and 0.2 g of anhydrous sodium acetate were added thereto. 0.15 g of bromine, dissolved in 2 ml of glacial acetic acid, was added dropwise to the mixture, while stirring. After the reaction had ended the mixture was poured over ice, and the precipitate thus obtained was recrystallized from ethanol. Melting point: 267°–272° C. (decomposition).

EXAMPLE 4

2-(2-Methoxy-4-methylsulfonyl-phenyl)-5H-imidazo[4,5-c]-pyridin-4-one 0.14 g of 2-(2-methoxy-4-methylmercapto-phenyl)-5H-imidazo[4,5-c]pyridin-4-one were dissolved in 10 ml of glacial acetic acid, the solution was mixed with 0.5 ml of 30% hydrogen peroxide, and the mixture was heated at 40°–50° C. for 2 hours. The reaction mixture was largely evaporated, the residue was mixed with ice water, and the precipitate thus obtained was suction-filtered off.

Melting point: 290° C. (decomposition).

EXAMPLE 5

2-(2-Methoxy-4-methylsulfinyl-phenyl)-5H-imidazo[4,5-c]pyridin-6-one

This compound was prepared analogous to Example 3 from 2-(2-methoxy-4-methylmercapto-phenyl)-5H-imidazo[4,5-c]pyridin-6-one.

EXAMPLE 6

2-(2-Methoxy-4-methylsulfonyl-phenyl)-5H-imidazo[4,5-c]pyridin-6-one

This compound was prepared analogous to Example 4 from 2-(2-methoxy-4-methyhlmercapto-phenyl)-5H-imidazo[4,5-c]pyridin-6-one.

EXAMPLE 7

2-(2-Propoxy-4-methylmercapto-phenyl)-5H-imidazo[4,5-c]pyridin-4-one hydrochloride This compound was prepared analogous to Example 2 from 2-propoxy-4-methylmercapto-benzoyl chloride and 2-methoxy-3,4-diamino-pyridine hydrochloride. Melting point: above 260° C.
Calculated: C-54.62%, H-5.16%; N-11.94% Found: C-54.60%; H-5.45%; N-11.95%.

EXAMPLE 8

2-(2-Methoxy-4-methylsulfinyl-phenyl)-5H-imidazo[4,5-c]pyridin-4-one and 2-(2-Methoxy-4-methylfulfonyl-phenyl)-5H-imidazo[4,5-c]pyridin-4-one 0.6 g of 2-(2-methoxy-4-methylmercapto-phenyl)-5H-imidazo[4,5-c]pyridin-4-one were stirred into 5 ml of glacial acetic acid, 0.5 ml of 35% hydrogen peroxide were added, and the mixture was stirred at room temperature for one and a half hours. The mixture was then diluted with water, neutralized with concentrated ammonia, evaporated and purified by chromatography on silica gel (eluant=methylene chloride/ethanol=9:1).
Yield of sulfinyl compounds: 0.18 g (28% of theory).
Melting point: 267°–272° C. (decomposition).
Yield of sulfonyl compound: 0.21 g (32% of theory).
Melting point: 290° C. (decomposition).

The compounds of the present invention, that is, those embraced by formula I above, their tautomers and their non-toxic, pharmacologically acceptable acid addition salts, have useful pharmacodynamic properties. More particularly, they exhibit hypotensive and positive inotropic activities in warm-blooded animals such as cats.

The above pharmacological properties were ascetained for the compounds of the present invention by the standard pharmacological test method described below, and the results of this test for a representative specie of the genus are shown in the table below, where A=2-(2-methoxy-4-methylmercapto-phenyl)-5H-imidazo-[4,5-c]-pyridin-6-one.

Determination of the effect on blood pressure and of the positive inotropic effect in the anesthetized cat The tests were carried out on cats which had been anesthetized with sodium pentobarbital (40 mg/kg i.p.). The animals breathed spontaneously. The arterial blood pressure was measured in the aorta abdominalis with a Statham pressure transducer (P 23 Dc). In order to determine the positive inotropic activity, the pressure in the left ventricle was measured with a catheter-tip manometer (Millar PC-350 A). From this the contractility parameter dp/dt was obtained, using an analog differentiator. The test compounds were injected into a vena femoralis. Polydiol 200 was used as the solvent. Each compound was tested on at least 3 cats.

The following table shows the average values:

| Compound | Dosage mg/kg i.v. | Increase in $dp/dt_{max}$ in % | Effect on blood pressure in mm Hg | Duration of activity (half life) in minutes |
|---|---|---|---|---|
| A | 2 | +143 | +41/+24 | 27 |

The compounds of the present invention are well tolerated, and no toxic effects on the heart or damage to the circulation of any kind were detected in these tests.

Based on their pharmacological properties the compounds of the present invention are useful for the treatment of cardiac insufficiencies of various origins since they increase the contractile force of the heart and facilitate the emptying of the heart by additionally lowering the blood pressure.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds according to the present invention is from 0.1 to 5 mg/kg body weight, one to four times daily.

The following examples illustrate a few pharmaceutical dosage unit compositions comprising a compound of the present invention as an active ingredient and represent the best modes contemplated of using the invention. The parts are parts by weight unless otherwise specified.

EXAMPLE 9

Tablets

The tablet composition is compounded from the following ingredients:

| | |
|---|---|
| 2-(2-Methoxy-4-methylmercapto-phenyl)-imidazo[4,5-c]pyridin-6-one | 100.0 parts |
| Lactose | 50.0 parts |
| Polyvinyl pyrrolidone | 5.0 parts |
| Carboxymethyl cellulose | 19.0 parts |
| Magnesium stearate | 1.0 parts |
| | 175.0 parts |

Preparation:
Moist screen: 1.5 mm.
Drying: Circulating air drier, 50° C.
Dry screen: 1 mm.
The remaining excipients are added to the granulate, and the finished mixture is compressed into 175 mg-tablets. Each tablet contains 100 mg of the active ingredient.

EXAMPLE 10

Coated tablets

The tablet core composition is compounded from the following ingredients;

| | |
|---|---|
| 2-(2-Methoxy-4-methylmercapto-phenyl)-imidazo[4,5-c]pyridin-6-one | 50.0 parts |
| Dried corn starch | 20.0 parts |

| | |
|---|---|
| Soluble starch | 2.0 parts |
| Carboxymethyl cellulose | 7.0 parts |
| Magnesium stearate | 1.0 parts |
| | 80.0 parts |

Preparation:

The active ingredient and the corn starch are uniformly moistened with an aqueous solution of the soluble starch.

Moist screen: 1.0 mm.
Dry screen: 1.0 mm.
Drying: 50° C. in a circulating air drier.

The granulate and other excipients are mixed together and compressed into 80 mg-tablet cores.

The finished cores are provided with a sugar coating in a coating pan in the usual way. Weight of the coated tablet: 120 mg. Each coated tablet contains 50 mg of the active ingredient.

EXAMPLE 11

Suppositories

The suppository composition is compounded from the following ingredients:

| | |
|---|---|
| 2-(2-Methoxy-4-methylmercapto-phenyl)-imidazo[4,5-c]-pyridin-6-one | 75.0 parts |
| Suppository base (e.g. cocoa butter) | 1625.0 parts |
| | 1700.0 parts |

Preparation:

The suppository base is melted. At 38° C. the finely ground active ingredient is homogeneously dispersed in the melt. The composition is cooled to 35° C., and 1700 mg-portions of it are poured into chilled suppository molds. Each suppository contains 75 mg of the active ingredient.

EXAMPLE 12

Hypodermic solution

The solution is compounded from the following ingredients:

| | |
|---|---|
| 2-(2-Methoxy-4-methylmercapto-phenyl)-imidazo[4,5-c]-pyridin-6-one | 50.0 parts |
| Ethoxylated hydroxystearic acid | 750.0 parts |
| 1,2-Propylene glycol | 1000.0 parts |
| Distilled water ad | 5000.0 parts by vol. |

Preparation:

The active ingredient is dissolved in 1,2-propylene glycol and ethoxylated hydroxystearic acid, the solution is diluted to the indicated volume with water, and filtered sterile.

Filling: in 5 ml ampules.
Sterilization: 20 minutes at 120° C.

EXAMPLE 13

Drop solution

The solution is compounded from the following ingredients:

| | |
|---|---|
| 2-(2-Methoxy-4-methylmercapto-phenyl)-imidazo[4,5-c]pyridin-6-one | 0.1 parts |
| Methyl p-hydroxybenzoate | 0.035 parts |
| Propyl p-hydroxybenzoate | 0.015 parts |
| Anisole | 0.05 parts |
| Menthol | 0.06 parts |
| Sodium saccharin | 1.0 parts |
| Glycerol | 10.0 parts |
| Ethanol | 40.0 parts |
| Distilled water ad | 100.0 parts by vol. |

Preparation:

The benzoates are dissolved in ethanol, and then the anisole and menthol are added. Then the active ingredient, glycerin and sodium saccharin dissolved in water are added. The solution is then filtered clear.

Any one of the other compounds embraced by formula I, a tautomer thereof or a non-toxic, pharmacologically acceptable acid addition salt thereof may be substituted for the particular active ingredient in Examples 9 through 13. Likewise, the amount of active ingredient in these illustrative examples may be varied to achieve the dosage unit range set forth above, and the amount and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

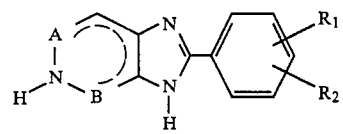

wherein one of A and B is methenyl and the other is carbonyl;

$R_1$ is (alkyl of 1 to 3 carbon atoms)mercapto, (alkyl of 1 to 3 carbon atoms)sulfinyl or (alkyl of 1 to 3 carbon atoms)sulfonyl; and $R_2$ is alkoxy of 1 to 3 carbon atoms;

a tautomer thereof, or a non-toxic, pharmacologically acceptable acid addition salt thereof.

2. A compound of claim 1,
wherein
$R_1$ is in the 4-position of the phenyl ring, and
$R_2$ is in the 2-position of the phenyl ring;
a tautomer thereof, or a non-toxic, pharmacologically acceptable acid addition salt thereof.

3. A compound of claim 2, which is 2-(2-methoxy-4-methylmercapto-phenyl)-5H-imidazo[4,5-c]pyridin-6-one, a tautomer thereof, or a non-toxic, pharmacologically acceptable acid addition salt thereof.

4. A cardiotonic pharmaceutical composition consisting essentially of an inert pharmaceutical carrier and an effective cardiotonic amount of a compound of claim 1.

5. The method of treating cardiac insufficiency in a warm-blooded animal in need thereof, which comprises perorally, parenterally or rectally administering to said animal an effective cardiotonic amount of a compound of claim 1.

* * * * *

UNITED STATES PATENT AND TRADEMARK OFFICE
CERTIFICATE OF CORRECTION

PATENT NO. : 4,568,680
DATED : Feb. 4, 1986
INVENTOR(S) : VOLKHARD AUSTEL ET AL.

It is certified that error appears in the above-identified patent and that said Letters Patent is hereby corrected as shown below:

Column 2, line 30: "at A'" should read -- of A' --.

Column 2, line 31: "alkoxymethyl" should read -- alkoxymethenyl --.

Column 4, line 11: "were purified" should read -- was purified --.

Column 5, line 7: "methyhlmercapto" should read -- methylmercapto --.

Column 5, line 47: "cetained" should read -- certained --.

Signed and Sealed this

Twenty-third Day of September 1986

[SEAL]

Attest:

DONALD J. QUIGG

Attesting Officer  Commissioner of Patents and Trademarks